(12) United States Patent  
Powers et al.

(10) Patent No.: US 7,959,591 B2  
(45) Date of Patent: Jun. 14, 2011

(54) DEVICE AND METHOD FOR EXTERNALLY ROTATING THE FEMUR

(75) Inventors: Christopher M. Powers, Marina del Rey, CA (US); Colin S. Gregersen, Cardiff by the Sea, CA (US); John Patrick Martin, Oceanside, CA (US)

(73) Assignee: DJO, LLC, Vista, CA (US)

( * ) Notice: Subject to any disclaimer, the term of this patent is extended or adjusted under 35 U.S.C. 154(b) by 4 days.

(21) Appl. No.: 11/376,652

(22) Filed: Mar. 15, 2006

(65) Prior Publication Data

US 2007/0219478 A1  Sep. 20, 2007

(51) Int. Cl.  
*A61F 13/06* (2006.01)  
*A61F 5/00* (2006.01)  
*A61F 5/37* (2006.01)  
*A61B 19/00* (2006.01)

(52) U.S. Cl. ............... 602/62; 602/61; 602/23; 602/26; 128/869; 128/882

(58) Field of Classification Search .............. 602/62, 602/26, 75, 13, 16, 63, 19, 60, 61, 23, 73; 224/661; 606/88, 56, 64, 212; 623/20.18; 600/595; 607/104; 128/869, 875, 876, 892, 128/96.1, 874, 98.1, 99.1, 100.1, 101.1, 102.1, 128/105.1, 882; 2/16, 22, 23, 338, 310, 311, 312; 450/86

See application file for complete search history.

(56) References Cited

U.S. PATENT DOCUMENTS

| 2,654,365 | A |  | 10/1953 | Whitaker |  |
|---|---|---|---|---|---|
| 2,753,864 | A |  | 7/1956 | Weidemann |  |
| 3,993,056 | A |  | 11/1976 | Rabischong et al. |  |
| 4,481,941 | A |  | 11/1984 | Rolfes |  |
| 4,602,627 | A |  | 7/1986 | Vito et al. |  |
| 5,107,827 | A | * | 4/1992 | Boyd | 602/58 |
| 5,230,700 | A |  | 7/1993 | Humbert et al. |  |
| 5,873,848 | A | * | 2/1999 | Fulkerson | 602/62 |
| 6,129,638 | A | * | 10/2000 | Davis | 473/215 |
| 6,428,495 | B1 | * | 8/2002 | Lynott | 602/23 |
| 2003/0009120 | A1 | * | 1/2003 | MacAllister | 602/23 |
| 2006/0000478 | A1 | * | 1/2006 | Taylor | 128/869 |

* cited by examiner

*Primary Examiner* — Patricia M Bianco  
*Assistant Examiner* — Ophelia Hawthorne  
(74) *Attorney, Agent, or Firm* — Ropes & Gray LLP

(57) ABSTRACT

An elongate flexible strap is adapted to be wrapped about a wearer's leg and pelvic region. The strap applies a torque to the leg, rotating the leg into a desired degree of external rotation. In a leg having an improperly aligned patella, it is believed that the external rotation improves lower extremity mechanics by aligning the patella within the trochlear groove.

23 Claims, 8 Drawing Sheets

DEVICE AND METHOD FOR EXTERNALLY ROTATING THE FEMUR

BACKGROUND OF THE INVENTION

1. Field of the Invention

The present invention relates to orthopedic devices for improving lower-extremity mechanics.

2. Description of the Related Art

Many people suffer from abnormal motions of the patella. There are several basic types of abnormalities that may occur with the patella: it may dislocate (slip out of place), sublux (partially slip out of place), fracture, develop degenerative arthritis, or develop a tracking problem. A tracking problem describes a patella that stays in place in front of the knee, but no longer remains centered in the front part of the femur known as the trochlear groove.

When tracking problems occur, the kneecap develops an abnormal set of biomechanics that results in abnormally increased pressure on the underside of the patella (patellar articular surface). The pain that results from this condition has a variety of different names, but all of these diagnoses refer to a biomechanical abnormality of the joint space between the patella and the trochlear groove of the femur. Normally, the patella sits centered in the groove.

One conventional treatment for patellar tracking problems comprises fitting the sufferer with an external brace. Many of these braces apply force directly to the patella in order to maintain it within the trochlear groove and to force it to follow the proper tracking path. For example, U.S. Pat. No. 4,296,744 to Palumbo discloses a dynamic patellar brace for both diagnosis and treatment of patellar subluxation. The brace includes a patellar bracing pad adapted to be positioned laterally with respect to the patella. The pad applies medially-directed pressure to the patella to help prevent subluxation.

SUMMARY OF THE INVENTION

The preferred embodiments of the present device and method for externally rotating the femur have several features, no single one of which is solely responsible for their desirable attributes. Without limiting the scope of this device and method as expressed by the claims that follow, their more prominent features will now be discussed briefly. After considering this discussion, and particularly after reading the section entitled "Detailed Description of the Preferred Embodiments," one will understand how the features of the preferred embodiments provide advantages, which include comfort, light weight, an unobtrusive appearance, and the ability to treat the causes of lower extremity dysfunction, rather than the symptoms.

Many people suffer from abnormal motions of the femur. These abnormal motions may be caused by hip muscle weakness, bony deformities of the hip (such as excessive anteversion), or a lack of lower extremity motor control. It is believed that these abnormal motions of the femur can sometimes cause a misalignment of the patella within the trochlear groove and/or patellar tracking problems, with subsequent patellofemoral joint pain. Therefore, one aspect of the present device and method for externally rotating the femur includes the realization that when correcting lower extremity mechanics, it is preferable to focus on the cause of any abnormal motion(s) (for example, abnormal motions of the femur), rather than to focus on the symptoms of the abnormal motion(s) (for example, misalignment of the patella). Accordingly, one embodiment of the present device and method applies a torque to the femur in order to externally rotate the femur.

With respect to a leg having a patella that is not properly aligned within the trochlear groove, it is believed that the externally rotated femur induces a proper alignment by moving the femur underneath the patella.

One embodiment of the present device and method for externally rotating the femur comprises a device for applying a torque to a wearer's leg. The torque moves the leg into external rotation to improve lower-extremity mechanics and align the patella with the trochlear groove. The device comprises an elongate flexible strap including a first portion, a second portion, a third portion, a fourth portion and a fifth portion. The first portion is adapted to engage the leg below the knee. The second portion is adapted to engage the leg along a medial side of the knee. The third portion is adapted to engage the leg above the knee. The fourth portion is adapted to extend along the thigh from a lower medial side thereof to an upper lateral side thereof. The fifth portion is adapted to engage the wearer's pelvic region.

Another embodiment of the present device and method for externally rotating the femur comprises a device for applying a torque to a wearer's leg. The torque moves the leg into external rotation to improve lower-extremity mechanics and align the patella with the trochlear groove. The device comprises an elongate flexible strap including a relatively long first portion. A second portion extends from an end of the first portion in a direction substantially perpendicular to the first portion. A third portion extends from an end of the second portion opposite the first portion in a direction substantially perpendicular to the second portion, substantially parallel to the first portion, and in a common direction with the first portion.

Another embodiment of the present device and method for externally rotating the femur comprises a device for applying a torque to a wearer's leg. The device comprises a first portion adapted to engage the leg in a region of the knee, a second portion adapted to extend around the thigh along a substantially helical path, and a third portion adapted to engage the wearer's pelvic region.

Another embodiment of the present device and method for externally rotating the femur comprises a method of moving a wearer's leg into external rotation. The method comprises the steps of securing to the leg in a region of the knee a first portion of a torquing device, applying a torque to the first portion by pulling a second portion of the torquing device in an upward and lateral direction, and securing a third portion of the device about the wearer's pelvic region to thereby maintain tension in the second portion.

BRIEF DESCRIPTION OF THE DRAWINGS

The preferred embodiments of the present device and method for externally rotating the femur, illustrating its features, will now be discussed in detail. These embodiments depict the novel and non-obvious device and method shown in the accompanying drawings, which are for illustrative purposes only. These drawings include the following figures, in which like numerals indicate like parts.

DETAILED DESCRIPTION OF THE PREFERRED EMBODIMENTS

Figure 1:
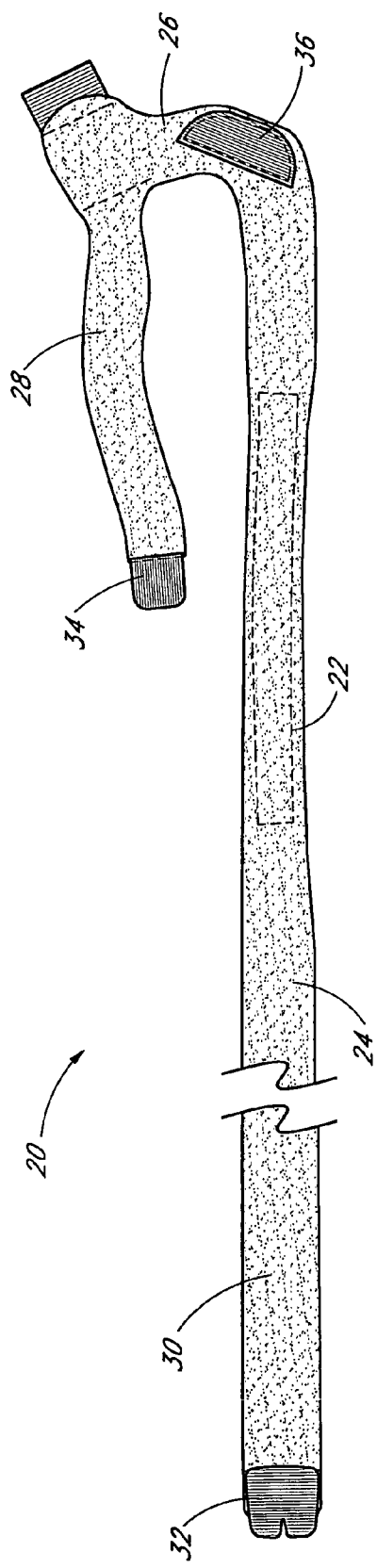
FIG. 1 is a top plan view of one embodiment of the present device for externally rotating the femur.
Figure 2:
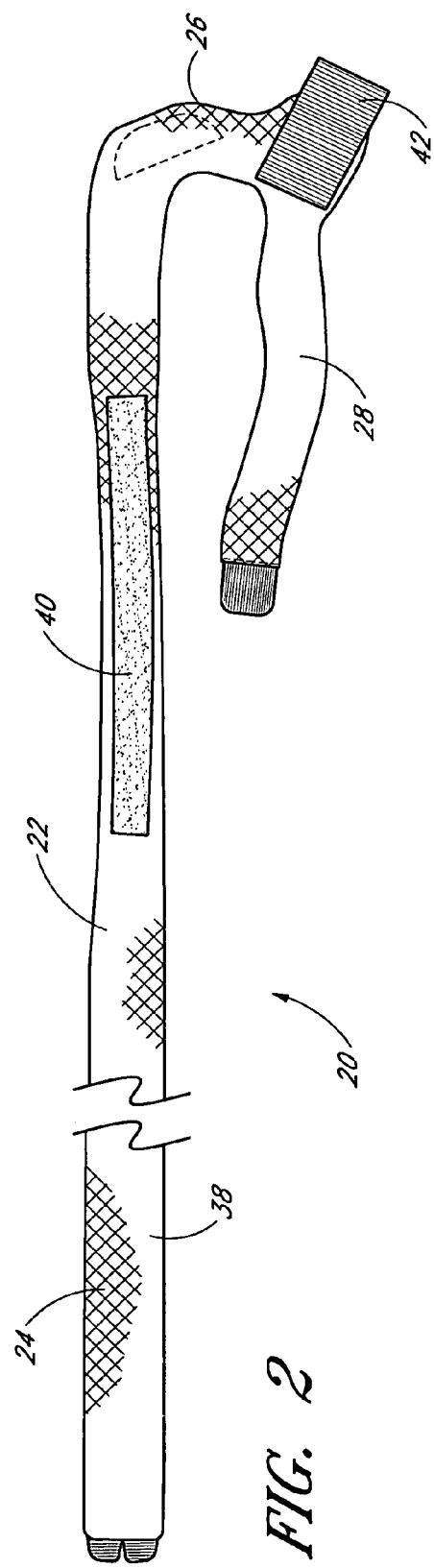
FIG. 2 is a bottom plan view of the device of FIG. 1.
Figure 3:
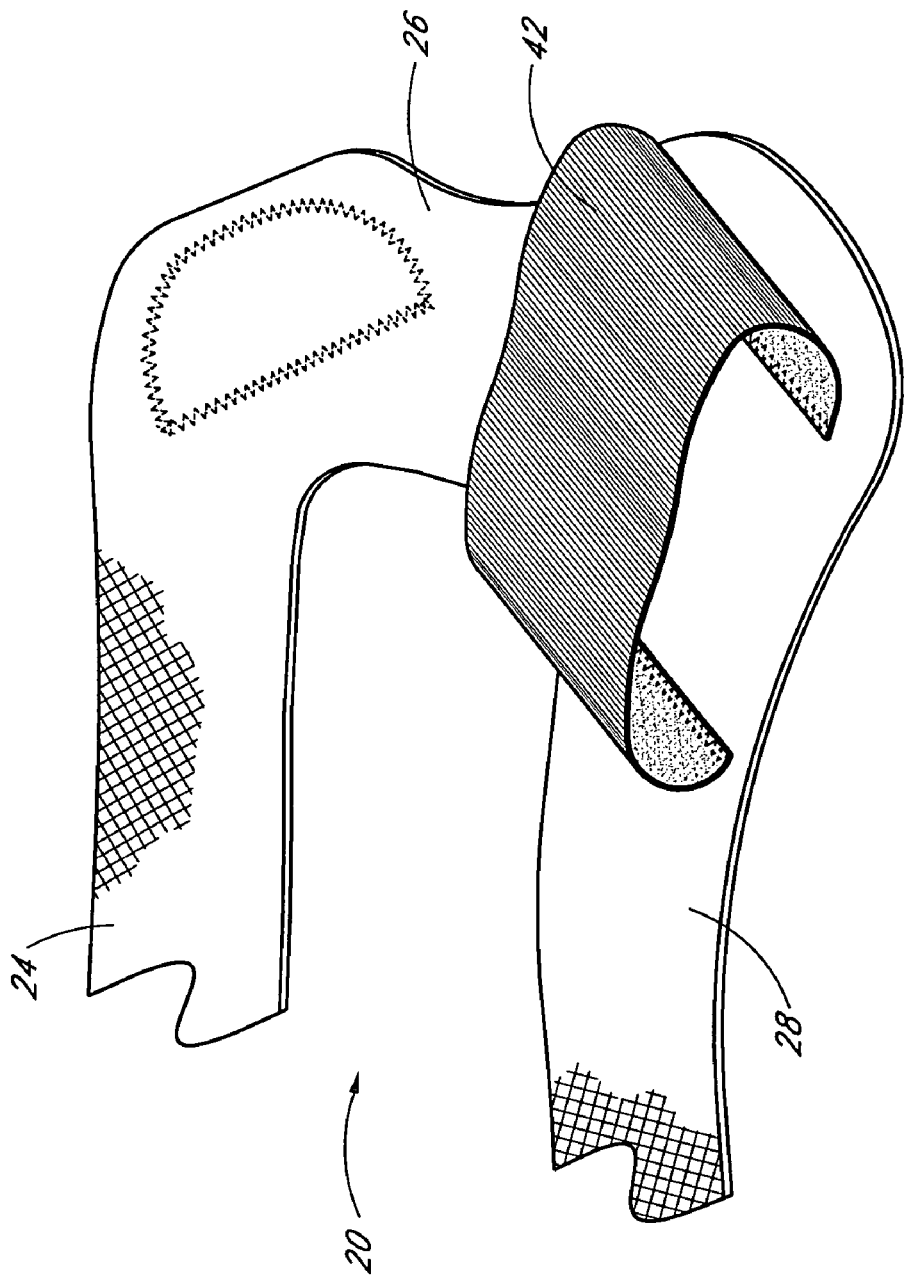
FIG. 3 is a detail bottom perspective view of the device of FIG. 1.

FIGS. 1-3 illustrate one embodiment of the present device 20 for externally rotating the femur. In these figures, the device 20 has been laid flat for ease of reference. The illustrated device 20 is adapted for wear on a left leg. However, those of ordinary skill in the art will appreciate that a device 20 having a mirrored configuration would be adapted for wear on a right leg. In fact, FIGS. 4-9 illustrate such a device having a mirrored configuration, and the steps for applying the device to a right leg.

The device 20 comprises a relatively thin, elongate strap 22 having a plurality of strap sections. In the flat configurations of FIGS. 1 and 2, the device 20 resembles a J. Thus, one section 24 of the strap 22 is substantially straight and is adapted to encircle the wearer's thigh and pelvis, as described in detail below. At one end, the thigh/pelvis strap section 24 adjoins a medial knee strap section 26 that extends substantially perpendicular to the thigh/pelvis strap section 24. The medial knee strap section 26 extends away from the thigh/pelvis strap section 24 and adjoins a calf strap section 28 that extends substantially perpendicular to the medial knee strap section 26, substantially parallel to the thigh/pelvis strap section 24, and in substantially the same direction as the thigh/pelvis strap section 24.

In FIGS. 1 and 2, the thigh/pelvis strap section 24 has been broken for ease of illustration. In one embodiment, this strap section is considerably longer than the remaining sections. For example, in one embodiment the thigh/pelvis strap section 24 is approximately 80 inches long, while the medial knee strap section 26 is approximately 10 inches long and the calf strap section 28 is approximately 18 inches long. Those of skill in the art will appreciate that the dimensions provided are merely one example, and should not be interpreted as limiting.

In the illustrated embodiment, the strap sections described above comprise a unitary piece of a flexible material. In some embodiments, the unitary flexible material may comprise several layers. For example, the strap 22 material may comprise a laminate of polyurethane foam and brushed nylon. In some embodiments, the strap 22 material may be durable, elastic, compressible and/or lightweight. Those of skill in the art will appreciate that the strap sections described above need not be constructed in a unitary fashion, and may be constructed separately and then secured together, for example by stitching.

With reference to FIG. 1, in the illustrated embodiment, a first surface, or outer surface 30, of the strap 22 comprises a loop material that is adapted to receive a hook material for releasable engagement. This outer surface 30 may be constructed of brushed nylon. The outer surface 30 faces away from the wearer when the device 20 is worn as described below. A plurality of hook material sections may be secured to the strap 22. For example, with reference to FIG. 1, an end of the thigh/pelvis strap section 24 opposite the medial knee strap section 26 may include a first patch 32 of hook material. A second patch 34 of hook material may be located at an end of the calf strap section 28 opposite the medial knee strap section 26, and a third patch 36 of hook material may be located at the junction of the thigh/pelvis strap section 24 and the medial knee strap section 26.

Each of the patches 32, 34, 36 may be releasably secured to the strap 22, or each may be permanently secured to the strap 22. For example, in FIGS. 1 and 2 the first patch 32 is releasably secured to the strap 22. The hook material on the first patch 32 engages the loop material on the outer surface 30 of the strap 22. A portion of the first patch 32 extends beyond the end of the thigh/pelvis strap section 24. This portion is adapted to be releasably secured to another portion of the strap 22 when the device 20 is applied to the wearer, as described below. The second patch 34 and third patch 46 are each permanently secured to the strap 22 with stitching. Those of ordinary skill in the art will appreciate that the patches may be secured to the strap 22 using alternative methods, such as snaps or buttons. Those of ordinary skill in the art will also appreciate that any of the patches may be permanently or releasably secured to the strap 22. The illustrated configuration is merely one example.

With reference to FIG. 2, a second surface, or inner surface 38, of the strap 22 comprises a relatively smooth material. The inner surface 38 faces the wearer's skin and/or clothing when the device 20 is worn as described below. Thus, the inner surface 38 may advantageously have a relatively high coefficient of static friction relative to human skin and most fabrics that people typically wear. The strap 22 is thus less prone to slip out of its intended position. In one embodiment, the inner surface 38 comprises polyurethane foam. However, those of ordinary skill in the art will appreciate that the inner surface 38 could be constructed of alternative materials, and that it need not necessarily have a high coefficient of static friction as described above.

With further reference to FIG. 2, a strip 40 of loop material is secured to the inner surface 38 of the strap 22 along the thigh/pelvis strap section 24. The loop material strip 40 may be secured to the inner surface 38 with stitching or any other means. The loop material strip 40 is located near the end of the thigh/pelvis strap section 24 that adjoins the medial knee strap section 26, and extends along approximately one-fifth of the length of the thigh/pelvis strap section 24. Those of ordinary skill in the art will appreciate that the relative lengths of the thigh/pelvis strap section 24 and the loop material strip 40 may be varied. In one embodiment, the loop material strip 40 is approximately 16 inches long. However, those of ordinary skill in the art will appreciate that the loop material strip 40 may be any length.

With reference to FIGS. 2 and 3, a calf-encircling band 42 is secured to the strap 22 near the junction of the thigh/pelvis strap section 24 and the medial knee strap section 26. The calf band 42 comprises a length of material sufficient to extend around at least a portion of the wearer's calf. The calf band 42 may be made from a flexible and elastic material. In one embodiment, the calf band 42 may be made of a composite of nylon, polyester and rubber. In the illustrated embodiment, opposite ends of the band 42 are secured to the strap 22 with stitching. Those of ordinary skill in the art will appreciate that the band may be secured to the strap 22 using alternative means, such as releasable fasteners.

Figure 4:
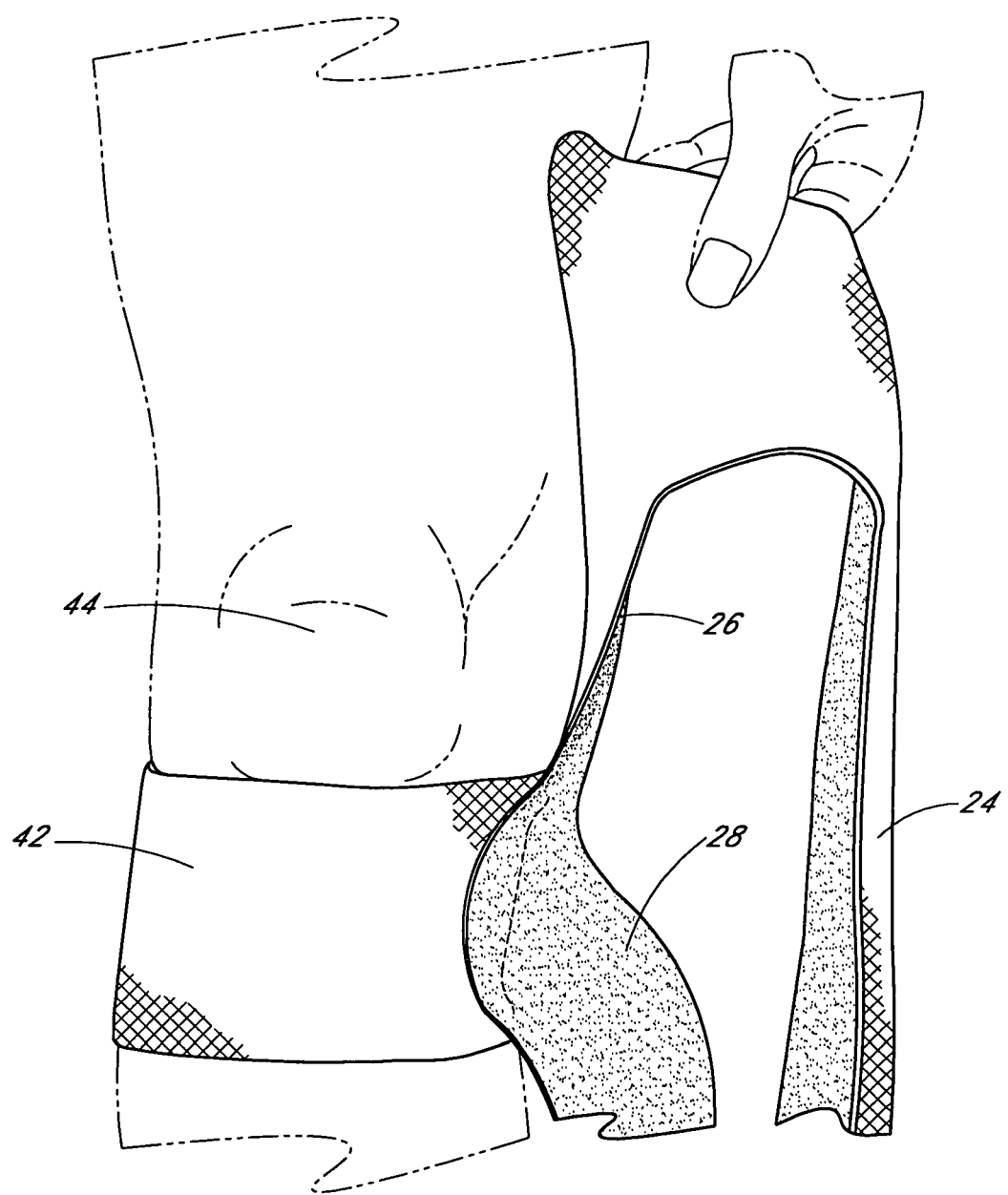
FIG. 4 is a front elevational view of a wearer's leg and the device of FIG. 1, illustrating one step of applying the device to the leg.

FIGS. 4-9 illustrate one method of externally rotating the femur using the present device 20. With reference to FIG. 4, the wearer begins by passing his or her foot through the calf band 42 and sliding the calf band 42 upward along the lower leg until the calf band 42 is positioned just below the knee 44. The medial knee strap section 26 should extend along the medial side of the wearer's leg above and below the knee. The calf strap section 28 should be located below the knee, and at least part of the thigh/pelvis strap section 24 should be located above the knee.

Figure 5:
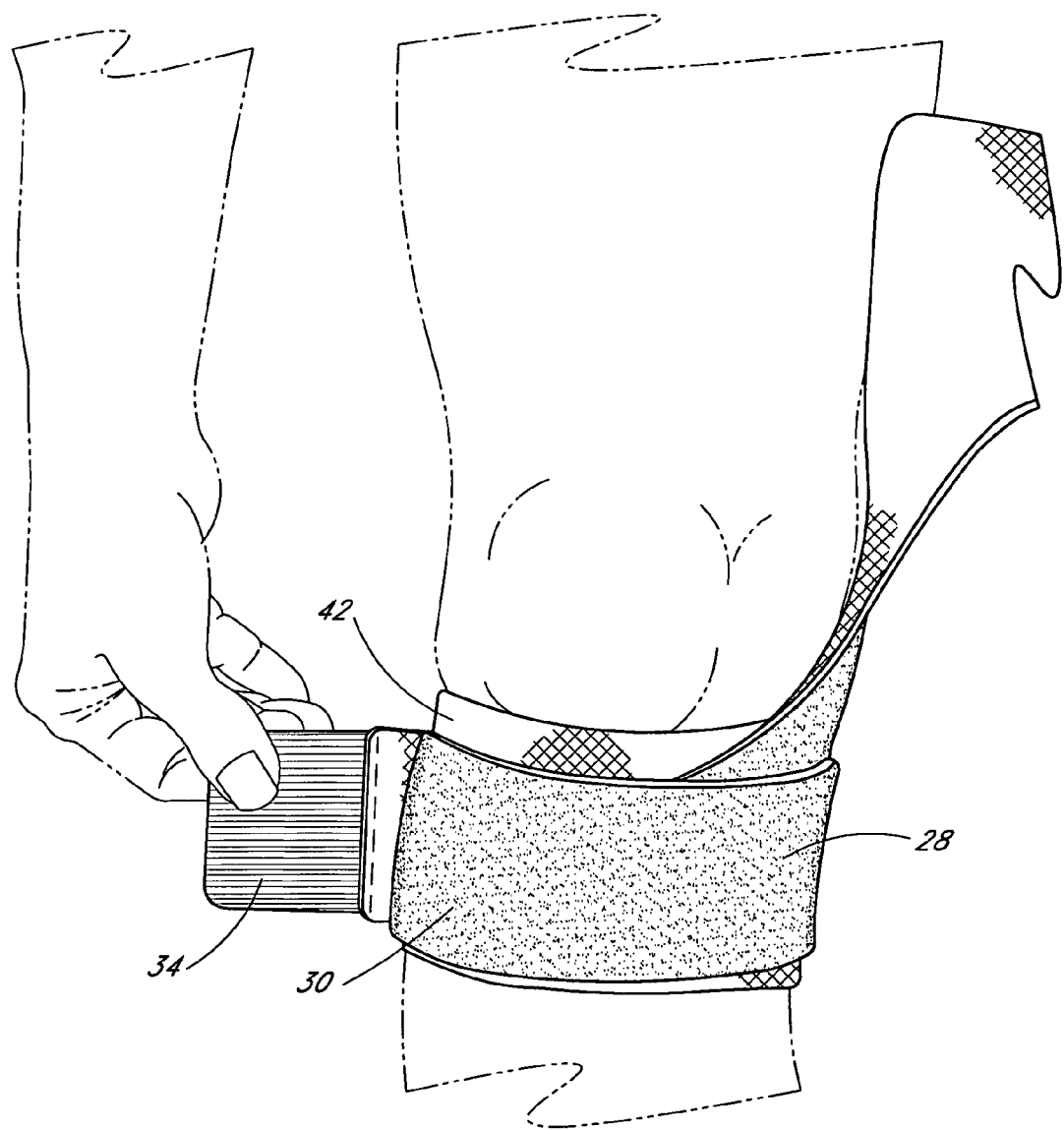
FIG. 5 is a front elevational view of the leg and the device of FIG. 4, illustrating another step of applying the device to the leg.
Figure 6:
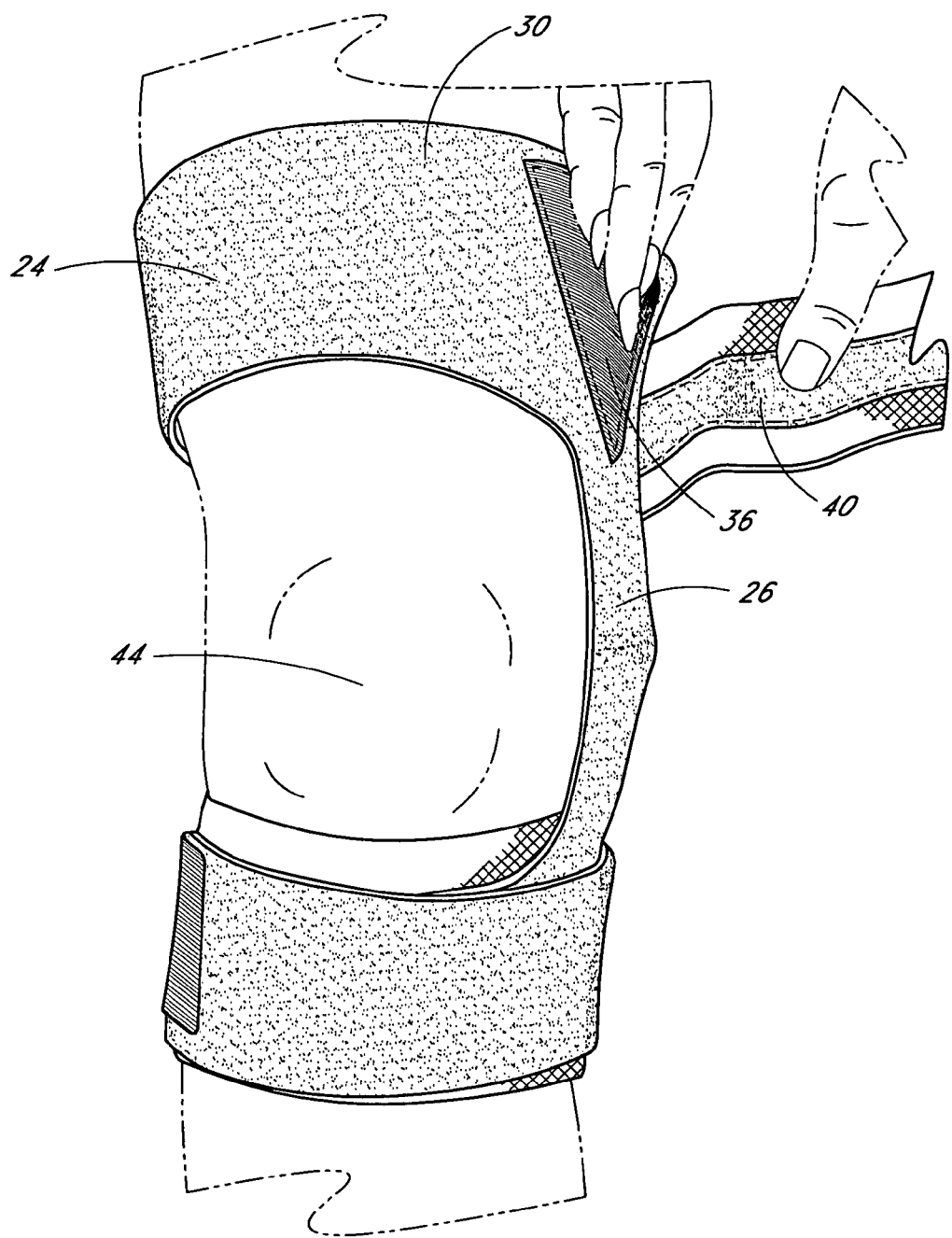
FIG. 6 is a front elevational view of the leg and the device of FIG. 4, illustrating another step of applying the device to the leg.
Figure 7:
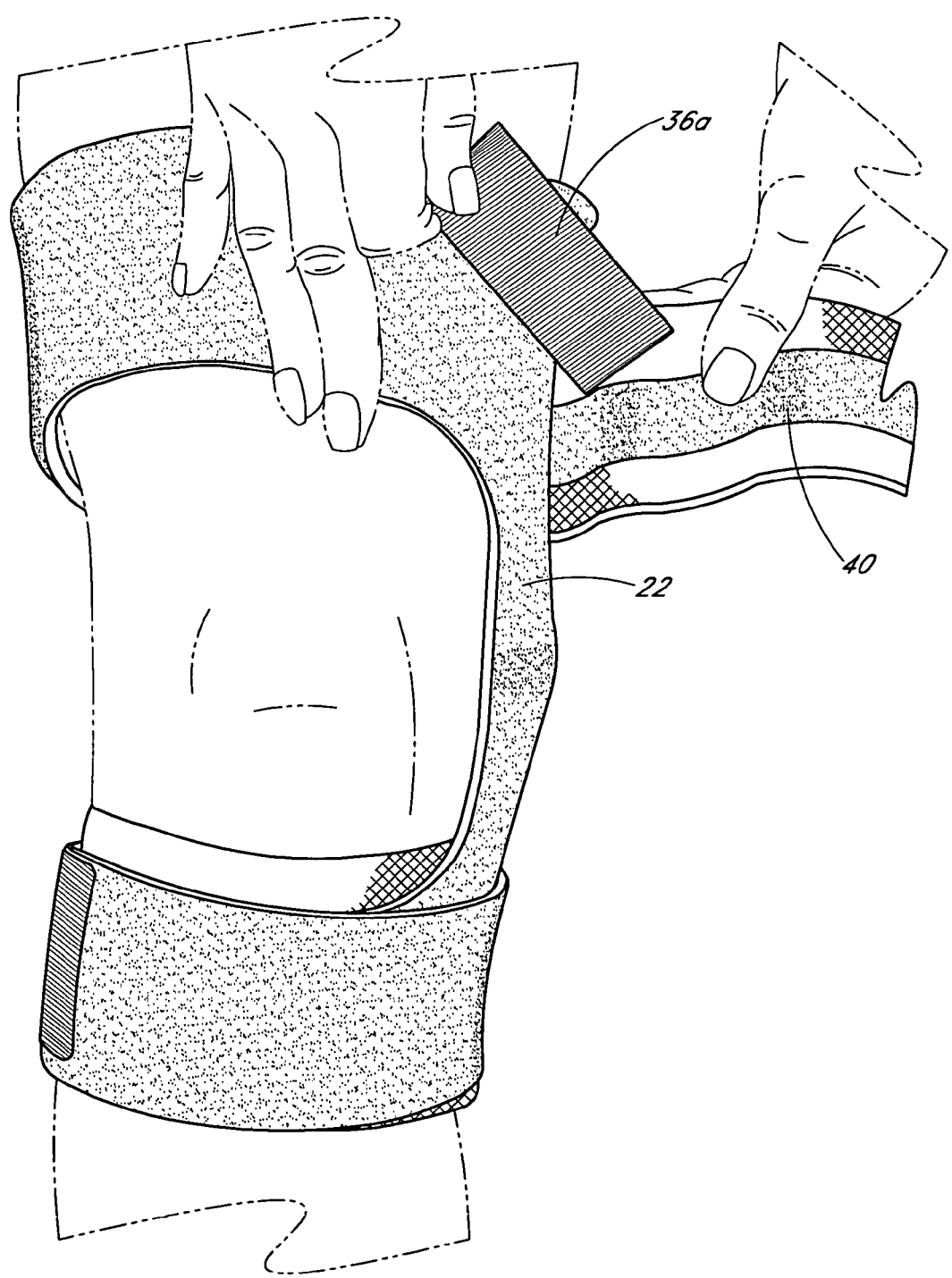
FIG. 7 is a front elevational view of the leg and the device of FIG. 4, illustrating another step of applying the device to the leg.

With reference to FIG. 5, the wearer next wraps the calf strap section 28 around his or her calf, over the calf band 42, and secures the second patch 34 of hook material to the outer surface 30 of the calf strap section 28. The wearer preferably applies sufficient tension to the calf strap section 28 to prevent migration while maintaining comfort for the wearer and not impeding circulation within the leg. With reference to FIG. 6, the wearer next wraps the thigh/pelvis strap section 24 across the anterior portion of his or her thigh just above the knee 44. The wearer continues wrapping the thigh/pelvis strap section 24 around the posterior portion of his or her thigh and back to the anterior portion. Using one hand, the wearer positions the junction of the medial knee strap section 26 and the thigh/pelvis strap section 24 so that it is located on the medial side of his or her leg above the knee. Using his or her other hand, the wearer then wraps the thigh/pelvis strap section 24 over the junction so that the loop material strip on the inner surface 38 of the strap 22 engages the third patch 36 of hook material on the outer surface 30 of the strap 22. As shown in FIG. 7, in one embodiment the third patch 36a may be removable and repositionable with respect to the strap 22. In this embodiment the wearer may reposition the third patch 36a for optimal engagement with the loop material strip 40. The wearer preferably applies tension to the thigh/pelvis strap section 24 before engaging the hook material to the loop material so that the thigh/pelvis strap 22 does not slip relative to the thigh. However, the tension should be light enough to maintain comfort for the wearer and not impede circulation within the leg. Furthermore, those of ordinary skill in the art will appreciate that neither the third patch 36, 36a nor the loop material strip 40 is essential to the proper functioning of the present device 20.

Figure 8:
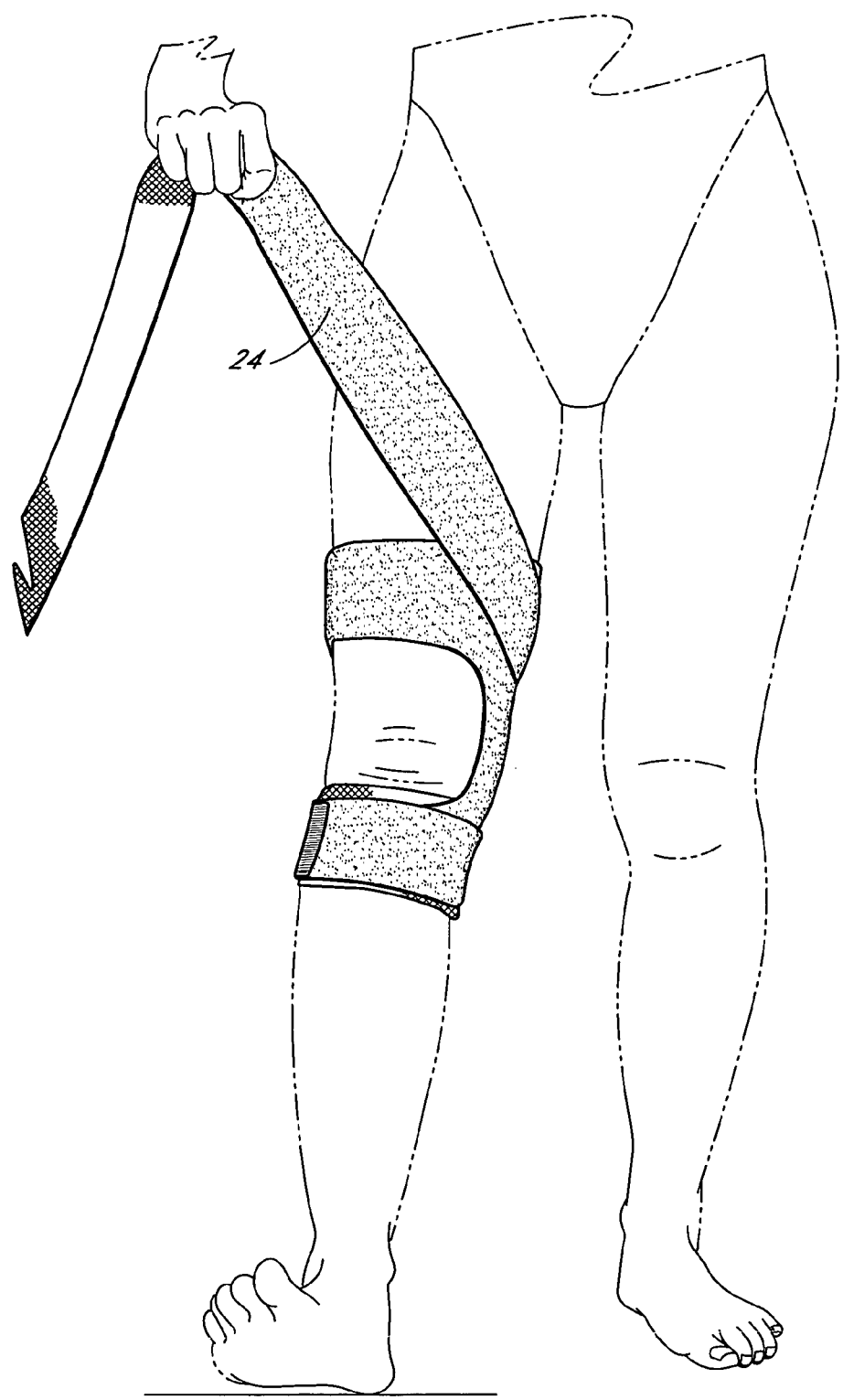
FIG. 8 is a front elevational view of the leg and the device of FIG. 4, illustrating another step of applying the device to the leg.

With reference to FIG. 8, the wearer next grasps the thigh/pelvis strap section 24 with his or her right hand (if the device 20 is being applied to the right leg), or with his or her left hand (if the device 20 is being applied to the left leg). Positioning his or her foot such that the heel rests on the floor and the toes are pointed slightly upward, the wearer pulls the thigh/pelvis strap section 24 upward and laterally. The pulling force applies a torque to the leg that moves the leg into external rotation. In one embodiment, the amount of external rotation may be within the range of 5° to 25° of external rotation, and may be within the range of 10° to 20° of external rotation in another embodiment. Finally, with reference to FIG. 9, the wearer wraps the thigh/pelvis strap section 24 diagonally upward and around his or her thigh following a substantially helical path, then around the waist, and secures the first patch of hook material to the outer surface 30 of the strap 22. In one embodiment, the strap 22 is located over the pelvis and greater trochanter, but below the iliac crest. However, those of ordinary skill in the art will appreciate that the strap 22 could be located higher or lower. The wearer preferably applies sufficient tension to the thigh/pelvis strap section 24 to maintain external rotation of the femur while maintaining comfort for the wearer and not impeding circulation.

Figure 9:
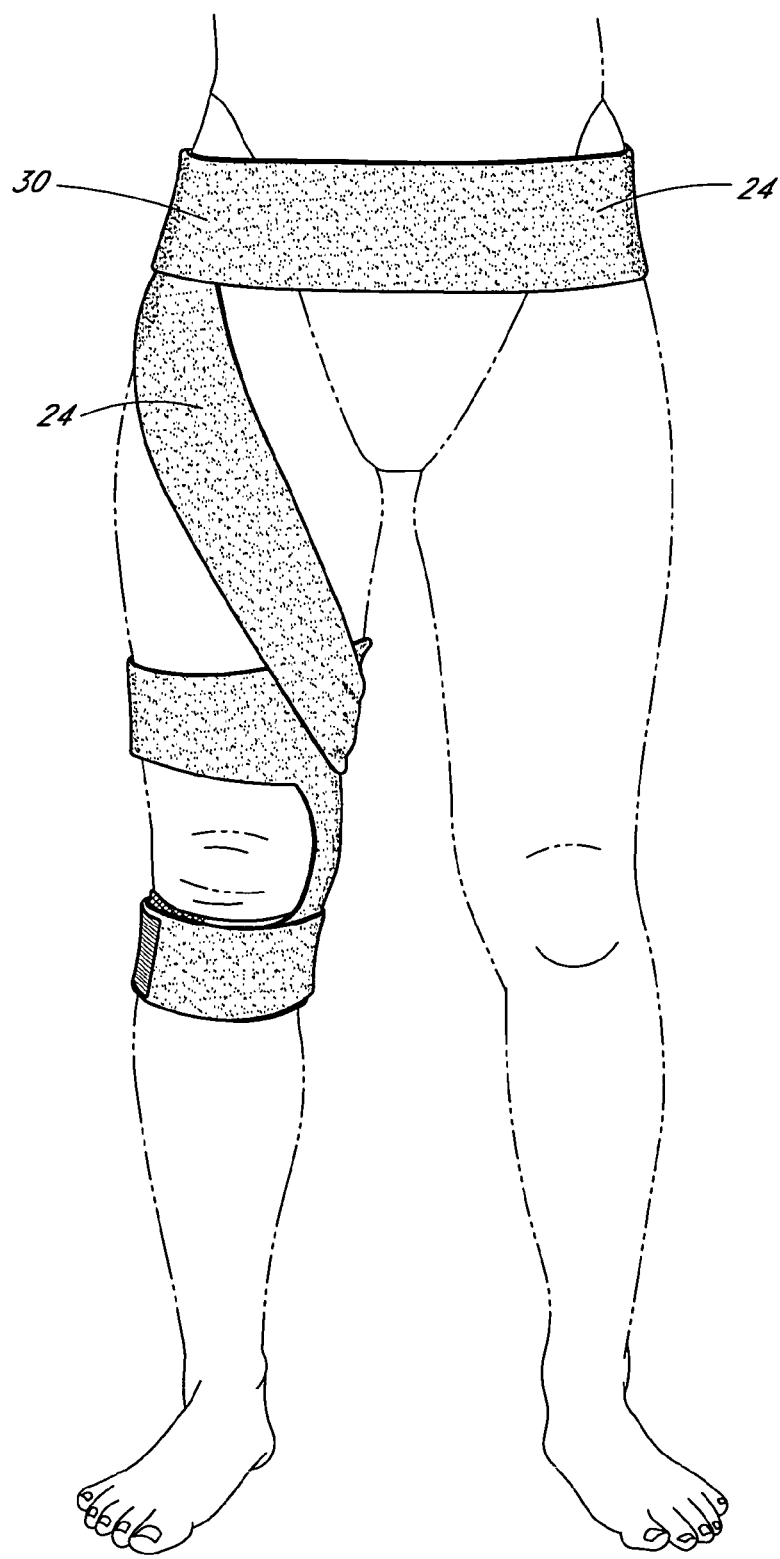
FIG. 9 is a front elevational view of the leg and the device of FIG. 4, illustrating the device applied to the leg and to the wearer's torso.

With the device 20 applied as shown in FIG. 9, the wearer's femur is external rotated while the patella remains stationary. Thus, the femur moves relative to the patella so that the patella becomes properly aligned with the trochlear groove. The device 20 is advantageously comfortable to wear, at least in part because of its light weight and flexibility. Further, the device comprises a flat strap with no rigid or protruding portions. Thus, it has an unobtrusive appearance that is easily hidden beneath clothing. The easy disguisability of the device means that a wearer need not feel any embarrassment over his or her need to wear an orthopedic appliance in public. The device 20 also provides effective treatment of patellofemoral misalignment, because it treats the cause of such misalignment (abnormal motions of the femur and tibia), rather than the symptoms.

SCOPE OF THE INVENTION

The above presents a description of the best mode contemplated for carrying out the present device and method for externally rotating the femur, and of the manner and process of making and using them, in such full, clear, concise, and exact terms as to enable any person skilled in the art to which it pertains to make and use this device and to practice this method. This device and this method are, however, susceptible to modifications and alternate constructions from that discussed above that are fully equivalent. Consequently, this device and this method are not limited to the particular embodiments disclosed. On the contrary, this device and this method each cover all modifications and alternate constructions coming within the spirit and scope of the device and method as generally expressed by the following claims, which particularly point out and distinctly claim the subject matter of the device and method.

What is claimed is:

1. A method of moving a wearer's leg into external rotation, the method comprising the steps of:
   positioning the wearer's foot proximate to a calf band that is joined to the interior surface of a torquing device;
   securing to the leg in a region below the knee a first portion of the torquing device that completely encircles the calf band and the region below the knee;
   securing a second portion of the torquing device along a medial side of the knee;
   applying a torque to the first portion and the second portion by pulling and positioning a third portion of the torquing device in an upward and lateral direction; and
   securing the third portion of the device about the wearer's pelvic region such that the third portion encircles the pelvic region to thereby maintain tension in the second portion.

2. The method of claim 1, wherein the torquing device comprises an elongate flexible strap.

3. The method of claim 2, wherein the step of securing the first portion to the leg comprises wrapping at least a segment of the first portion about the leg and securing an end of the first portion at an intermediate location on the first portion.

4. The method of claim 2, wherein the step of securing the third portion about the wearer's pelvic region comprises wrapping at least a segment of the third portion about the wearer's pelvic region and securing an end of the third portion at an intermediate location on the third portion.

5. A device for applying a torque to a wearer's leg, the torque moving the leg into external rotation to thereby improve lower-extremity mechanics and align the patella with the trochlear groove, the device comprising:
   an elongate flexible strap including a first portion, a second portion, a third portion, a fourth portion and a fifth portion;

wherein the first portion completely encircles the leg below the knee along a calf of the wearer's leg, the second portion extends upwardly from the first portion along a medial side of the knee, the third portion encircles the wearer's leg above the knee, the fourth portion extends along the thigh from a lower medial side thereof to an upper lateral side thereof, the fifth portion encircles the wearer's pelvic region, and a calf band that underlies the first portion of the elongate flexible strap.

6. The device of claim 5, wherein the third portion completely encircles the wearer's leg.

7. The device of claim 5, wherein the fifth portion completely encircles the wearer's pelvic region.

8. The device of claim 5, wherein at least a portion of an outer surface of the strap comprises a loop material.

9. The device of claim 5, wherein at least a portion of an inner surface of the strap comprises a loop material.

10. The device of claim 5, further comprising a portion of hook material located at or near a junction of the second portion and the third portion.

11. The device of claim 5, further comprising a portion of hook material located at an end of the first portion.

12. The device of claim 5, further comprising a portion of hook material located at an end of the fifth portion.

13. The device of claim 5, wherein at least a portion of the strap is elastic.

14. A device for applying a torque to a wearer's leg, the torque moving the leg into external rotation to thereby improve lower-extremity mechanics and align the patella with the trochlear groove, the device comprising:

an elongate flexible strap including a first portion, a second portion extending from an end of the first portion in a direction substantially perpendicular to the first portion, and a third portion extending from an end of the second portion opposite the first portion in a direction substantially perpendicular to the second portion, substantially parallel to the first portion, and in a common direction with the first portion, wherein the first portion is longer than either of the second portion and the third portion and a portion of the first portion encircles the wearer's pelvic region.

15. The device of claim 14, further comprising an elastic band located at or near a junction of the second portion and the third portion.

16. The device of claim 14, further comprising a portion of hook material located at or near a junction of the first portion and the second portion.

17. The device of claim 14, further comprising a portion of hook material located at an end of the first portion.

18. The device of claim 14, further comprising a portion of hook material located at an end of the third portion.

19. The device of claim 14, wherein at least a portion of the strap is elastic.

20. The device of claim 14, wherein at least a portion of an outer surface of the strap comprises a loop material.

21. The device of claim 14, wherein the third portion is at least twice as long as the first portion.

22. The device of claim 14, wherein the third portion is approximately 8 times as long as the first portion.

23. The device of claim 14, wherein the flexible strap resembles a J in a flat configuration.

* * * * *